(12) United States Patent
Calanca et al.

(10) Patent No.: US 10,376,878 B2
(45) Date of Patent: Aug. 13, 2019

(54) DEVICES, APPARATUS, KIT AND METHOD FOR TREATING A BIOLOGICAL SAMPLE

(71) Applicant: Menarini Silicon Biosystems S.p.A., Castel Maggiore (IT)

(72) Inventors: Alex Calanca, Mirandola (IT); Gianni Medoro, Casalecchio di Reno (IT); Nicolò Manaresi, Bologna (IT); Giuseppe Giorgini, Padua (IT)

(73) Assignee: Menarini Silicon Biosystems S.p.A., Castel Maggiore (IT)

( * ) Notice: Subject to any disclaimer, the term of this patent is extended or adjusted under 35 U.S.C. 154(b) by 537 days.

(21) Appl. No.: 14/369,221

(22) PCT Filed: Dec. 28, 2012

(86) PCT No.: PCT/IB2012/057797
§ 371 (c)(1),
(2) Date: Jun. 27, 2014

(87) PCT Pub. No.: WO2013/098792
PCT Pub. Date: Jul. 4, 2013

(65) Prior Publication Data
US 2015/0031040 A1    Jan. 29, 2015

(30) Foreign Application Priority Data

Dec. 28, 2011    (IT) .............................. BO2011A0766

(51) Int. Cl.
*B01L 3/00*    (2006.01)
*C12Q 1/686*    (2018.01)
*G01N 1/40*    (2006.01)

(52) U.S. Cl.
CPC ............ *B01L 3/5021* (2013.01); *C12Q 1/686* (2013.01); *G01N 1/4077* (2013.01);
(Continued)

(58) Field of Classification Search
None
See application file for complete search history.

(56) References Cited

U.S. PATENT DOCUMENTS 4,682,007 A    7/1987    Hollander
4,956,298 A    9/1990    Diekmann
(Continued)

FOREIGN PATENT DOCUMENTS

DE    3931851 C2    4/1992
DE    10203636 B4    2/2004
(Continued)

OTHER PUBLICATIONS

Altomare et al., Levitation and movement of human tumor cells using a printed circuit board device based on software-controlled dielectrophoresis, Biotechnol. Bioeng., 82(4):474-9 (2003).
(Continued)

*Primary Examiner* — Jill A Warden
*Assistant Examiner* — Dwayne K Handy
(74) *Attorney, Agent, or Firm* — Marshall, Gerstein & Borun LLP (57) ABSTRACT

Method for the treatment of a biological sample comprising at least one cell and a liquid component; according to the method, a force is applied to the sample inserted in an inner chamber of a hollow device towards a filter which has pores with diameters from 2 nm to 1 μm, so that at least part of the liquid component passes through the filter and the cell remains in the inner chamber, thus obtaining a concentrated sample; the filter has a surface facing the inner chamber of less than 12.6 mm².

23 Claims, 4 Drawing Sheets

(52) U.S. Cl.
CPC . *B01L 2200/0631* (2013.01); *B01L 2300/042* (2013.01); *B01L 2300/0681* (2013.01); *B01L 2300/0832* (2013.01); *B01L 2400/0409* (2013.01); *G01N 2001/4088* (2013.01); *Y10T 436/25375* (2015.01)

(56) References Cited

U.S. PATENT DOCUMENTS

| | | |
|---|---|---|
| 4,990,253 A | 2/1991 | Vcelka |
| 5,252,493 A | 10/1993 | Fujiwara et al. |
| 5,279,493 A | 1/1994 | Halder |
| 5,556,598 A | 9/1996 | Raybuck et al. |
| 5,833,860 A | 11/1998 | Kopaciewicz et al. |
| 5,888,370 A | 3/1999 | Becker et al. |
| 5,942,443 A | 8/1999 | Parce et al. |
| 5,945,281 A | 8/1999 | Prabhu |
| 6,149,789 A | 11/2000 | Benecke et al. |
| 6,203,683 B1 | 3/2001 | Austin et al. |
| 6,264,815 B1 | 7/2001 | Pethig et al. |
| 6,294,063 B1 | 9/2001 | Becker et al. |
| 6,824,664 B1 | 11/2004 | Austin et al. |
| 6,830,729 B1 | 12/2004 | Holl et al. |
| 6,875,329 B2 | 4/2005 | Washizu et al. |
| 6,888,721 B1 | 5/2005 | Moghaddam et al. |
| 6,911,132 B2 | 6/2005 | Pamula et al. |
| 6,977,033 B2 | 12/2005 | Becker et al. |
| 7,147,763 B2 | 12/2006 | Elrod et al. |
| 7,250,933 B2 | 7/2007 | De Boer et al. |
| 7,307,328 B2 | 12/2007 | Meyer et al. |
| 7,488,406 B2 | 2/2009 | Hughes et al. |
| 7,641,779 B2 | 1/2010 | Becker et al. |
| 8,216,513 B2 | 7/2012 | Becker et al. |
| 8,349,160 B2 | 1/2013 | Medoro et al. |
| 8,388,823 B2 | 3/2013 | Manaresi et al. |
| 8,641,880 B2 | 2/2014 | Medoro et al. |
| 8,679,856 B2 | 3/2014 | Manaresi |
| 8,685,217 B2 | 4/2014 | Manaresi et al. |
| 9,310,287 B2 | 4/2016 | Medoro et al. |
| 2002/0031838 A1 | 3/2002 | Meinhart et al. |
| 2002/0036139 A1 | 3/2002 | Becker et al. |
| 2002/0070114 A1 | 6/2002 | Miles |
| 2002/0125138 A1 | 9/2002 | Medoro |
| 2002/0132316 A1 | 9/2002 | Wang et al. |
| 2002/0172987 A1 | 11/2002 | Terstappen et al. |
| 2002/0195342 A1 | 12/2002 | Lee et al. |
| 2003/0044832 A1 | 3/2003 | Blankenstein |
| 2003/0047456 A1 | 3/2003 | Medoro |
| 2003/0069413 A1 | 4/2003 | Pai et al. |
| 2003/0073110 A1 | 4/2003 | Aritomi et al. |
| 2003/0098271 A1 | 5/2003 | Somack et al. |
| 2004/0011652 A1 | 1/2004 | Bressler |
| 2004/0055891 A1 | 3/2004 | Pamula et al. |
| 2004/0058450 A1 | 3/2004 | Pamula et al. |
| 2004/0063196 A1 | 4/2004 | Muller et al. |
| 2004/0159546 A1 | 8/2004 | Zhang et al. |
| 2004/0191789 A1 | 9/2004 | Manaresi et al. |
| 2004/0209354 A1 | 10/2004 | Mathies et al. |
| 2004/0229210 A1 | 11/2004 | Sabry et al. |
| 2005/0009101 A1 | 1/2005 | Blackburn |
| 2005/0014146 A1 | 1/2005 | Manaresi et al. |
| 2005/0112541 A1 | 5/2005 | Durack et al. |
| 2005/0214736 A1 | 9/2005 | Childers et al. |
| 2006/0029923 A1* | 2/2006 | Togawa .............. B01D 61/18 435/2 |
| 2006/0037903 A1* | 2/2006 | Smith .............. B01L 3/5021 210/240 |
| 2006/0051775 A1 | 3/2006 | Bianchi |
| 2006/0057738 A1* | 3/2006 | Hall, Jr. .............. G01N 1/38 436/177 |
| 2006/0072804 A1 | 4/2006 | Watson et al. |
| 2006/0086309 A1 | 4/2006 | Manger et al. |
| 2006/0139638 A1 | 6/2006 | Muller et al. |
| 2006/0177815 A1 | 8/2006 | Soh et al. |
| 2006/0223178 A1 | 10/2006 | Barber et al. |
| 2006/0228749 A1 | 10/2006 | Wang et al. |
| 2006/0290745 A1 | 12/2006 | Feng et al. |
| 2007/0015289 A1 | 1/2007 | Kao et al. |
| 2007/0026413 A1 | 2/2007 | Toner et al. |
| 2007/0026415 A1 | 2/2007 | Fuchs et al. |
| 2007/0051412 A1 | 3/2007 | Heath et al. |
| 2007/0059683 A1 | 3/2007 | Barber et al. |
| 2007/0172903 A1 | 7/2007 | Toner et al. |
| 2007/0190522 A1 | 8/2007 | Somack et al. |
| 2007/0195324 A1 | 8/2007 | Adams et al. |
| 2007/0250301 A1 | 10/2007 | Vaisberg et al. |
| 2008/0057572 A1 | 3/2008 | Petersen et al. |
| 2008/0058991 A1 | 3/2008 | Lee et al. |
| 2008/0246489 A1 | 10/2008 | Coster et al. |
| 2008/0264068 A1 | 10/2008 | Nakasuka et al. |
| 2009/0205963 A1 | 8/2009 | Medoro et al. |
| 2009/0218223 A1 | 9/2009 | Manaresi et al. |
| 2009/0288963 A1 | 11/2009 | Guerrieri et al. |
| 2010/0035292 A1 | 2/2010 | Levhenko et al. |
| 2010/0043575 A1 | 2/2010 | Tajima |
| 2010/0248285 A1 | 9/2010 | Manaresi |
| 2010/0331205 A1 | 12/2010 | Medoro |
| 2011/0003380 A1 | 1/2011 | Miltenyi et al. |
| 2011/0183433 A1 | 7/2011 | Motadel et al. |
| 2011/0193006 A1 | 8/2011 | Simone et al. |
| 2012/0071335 A1 | 3/2012 | Manaresi et al. |
| 2012/0091001 A1 | 4/2012 | Manaresi et al. |
| 2012/0184010 A1 | 7/2012 | Medoro et al. |
| 2013/0118903 A1 | 5/2013 | Becker et al. |
| 2014/0131207 A1 | 5/2014 | Medoro et al. |
| 2014/0315236 A1 | 10/2014 | Manaresi |
| 2015/0126396 A1 | 5/2015 | Manaresi et al. |

FOREIGN PATENT DOCUMENTS

| | | |
|---|---|---|
| DE | 19500660 B4 | 12/2007 |
| EP | 0 500 727 A1 | 9/1992 |
| EP | 1145766 B1 | 8/2007 |
| EP | 1304388 B1 | 2/2008 |
| EP | 1179585 B1 | 7/2008 |
| EP | 2260943 A1 | 12/2010 |
| JP | 58211272 | 12/1983 |
| JP | 2000292480 A | 10/2000 |
| JP | 2002503334 A | 1/2002 |
| JP | 2002311461 A | 10/2002 |
| JP | 2002536167 A | 10/2002 |
| JP | 2003121886 A | 4/2003 |
| JP | 2003202604 A | 7/2003 |
| JP | 2004000935 A | 1/2004 |
| JP | 2005501296 A | 1/2005 |
| JP | 2005507997 A | 3/2005 |
| JP | 2005510705 A | 4/2005 |
| JP | 2005176836 A | 7/2005 |
| JP | 2005257283 A | 9/2005 |
| JP | 2005304445 A | 11/2005 |
| JP | 2006504974 A | 2/2006 |
| JP | 2006512092 A | 4/2006 |
| JP | 2006517024 A | 7/2006 |
| JP | 2007017163 | 1/2007 |
| JP | 2008533487 | 8/2008 |
| JP | 60071935 | 4/2015 |
| WO | WO-91/07660 | 5/1991 |
| WO | WO-91/08284 | 6/1991 |
| WO | WO-98/04355 | 2/1998 |
| WO | WO-99/17883 | 4/1999 |
| WO | WO-00/28313 | 5/2000 |
| WO | WO-00/47322 | 8/2000 |
| WO | WO-00/69525 | 11/2000 |
| WO | WO-00/69565 | 11/2000 |
| WO | WO-01/21311 A1 | 3/2001 |
| WO | WO-02/12896 | 2/2002 |
| WO | WO-02/41999 A1 | 5/2002 |
| WO | WO-02/088702 A2 | 11/2002 |
| WO | WO-03/014739 | 2/2003 |
| WO | WO-03/035895 | 5/2003 |
| WO | WO-03/045556 | 6/2003 |
| WO | WO-2004/030820 | 4/2004 |
| WO | WO-2004/071668 | 8/2004 |
| WO | WO-2005/098395 | 10/2005 |
| WO | WO-2006/003214 | 1/2006 |

(56) References Cited

FOREIGN PATENT DOCUMENTS

| WO | WO-2006/008602 | 1/2006 |
|----|----|----|
| WO | WO-2006/018849 | 2/2006 |
| WO | WO-2007/010367 | 1/2007 |
| WO | WO-2005/060432 | 3/2007 |
| WO | WO-2007/049103 | 5/2007 |
| WO | WO-2007/049120 | 5/2007 |
| WO | WO-2007/110739 | 10/2007 |
| WO | WO-2007/116312 | 10/2007 |
| WO | WO-2007/147018 | 12/2007 |
| WO | WO-2007/147076 | 12/2007 |
| WO | WO-2008/011274 | 1/2008 |
| WO | WO-2008/131035 | 10/2008 |
| WO | WO-2009/022222 | 2/2009 |
| WO | WO-2010/106426 | 9/2010 |
| WO | WO-2010/106434 | 9/2010 |
| WO | WO-2010/149292 | 12/2010 |

OTHER PUBLICATIONS

Berthier et al., NSTI Nanotech 2005, vol. 1 (2005), www.nsti.org.
Bonci et al., The miR-15a-miR-16-1 cluster controls prostate cancer by targeting multiple oncogenic activities, Nat. Med., 14:1271-7 (2008).
Cheung et al., Impedance spectroscopy flow cytometry: on-chip label-free cell differentiation, Cytometry Part A, 65A(2):124-32 (2005).
Diamond et al., Flow cytometry in the diagnosis and classification of malignant lymphome and leukemia, Cancer, 50:1122-35 (1982).
de Bono et al., Circulating tumor cells predict survival benefit from treatment in metastatic castration-resistant prostate cancer, Clin. Cancer Res., 14(19):6302-9 (2008).
Fiedler et al., Dielectrophoretic sorting of particles and cells in a microsystem, Anal. Chem., 80(9):1909-15 (1998).
Fiedler et al., Electrocasting formation and structuring of suspended microbodies using A.C. generated field cages, Microsystem Technologies, Berlin, Germany, pp. 1-7 (Dec. 1, 1995).
Fuchs et al., Electronic sorting and recovery of single live cells from microlitre sized samples, Lab Chip, 6:121-6 (2006).
Fuhr et al., Positioning and manipulation of cells and microparticles using miniturized electric field traps and travelling waves, Sensors and Materials, 7(2):131-46 (1995).
Gascoyne et al., Dielectrophoresis-based programmable fluidic processors, Lab Chip, 4:299-304 (2004).
Gascoyne et al., Particle separation by dielectrophoresis, Electrophoresis, 23(13): 1973-83 (2002).
Green et al., Ac Electrokinetics: a survey of sub-micrometre particle dynamics, J. Phys. D: Appl. Phys., 33:632-41 (Dec. 10, 1999).
Hughes, Strategies for dielectrophoretic separation in laboratory-on-a-chip systems, Electrophoresis, 23(16): 2569-82 (2002).
International Search Report and Written Opinion, corresponding International Application No. PCT/IB2012/057797, dated May 8, 2013.
Jones, An electromechanical interpretation of electrowetting, J. Micromech. Microeng., 15(6):1184-7 (2005).
Klein et al., Comparative genomic hybridization, loss of heterozygosity, and DNA sequence analysis of single cells, Proc. Natl. Acad. Sci. USA, 96(8):4494-9 (1999).
Long et al., A new preprocessing approach for cell recognition, IEEE Trans. Information Tech. Biomed., 9(3):407-12 (2005).
Manaresi et al., A CMOS chip for individual cell manipulation and detection, IEEE Journal of Solid-State Circuits, 38 (12):2297-305 (2003).
Medoro et al., A lab-on-a-chip for cell detection and manipulation, IEEE Sensors Journal, 3(3):317-25 (2003).
Medoro et al., A lab-on-a-chip for cell separation based on the moving-cages approach, Proceedings of the 16th Conference on Solid State Transducers, pp. 500-501 (Sep. 15, 2002).
Medoro et al., Dielectrophoretic cage-speed separation of bioparticles, Sensors, Proceedings of the IEEE Vienna, Austria, Oct. 24-27, 2004, pp. 76-79.
Milner et al., Dielectrophoretic classification of bacteria using differential impedance measurements, Electronics Letters, 34(1):66-8 (1998).
Nagrath et al., Isolation of rare circulating tumour cells in cancer patients by microchip technology, Nature, 450(7173):1235-9 (2007).
Nieuwenhuis et al., Near-field optical sensors for particle shape measurements, Sensors Journal IEEE, 3(5):646-51 (2003).
O'Hara et al., Ratcheting electrophoresis microchip (REM) for programmable transport and separation of macromolecules, Proceedings of the International Mechanical Engineering Congress and Exposition, 3:619-28 (2001).
Ohta et al., Tech. Dig. of the Solid State Sensor, Actuator and Microsystems, Workshop, pp. 216-219 (2004).
Petersson et al., Carrier medium exchange through ultrasonic particle switching in microfluidic channels, Anal. Chem., 77:1216-21 (2005).
Pethig et al., Enhancing traveling-wave dielectrophoresis with signal superposition, IEEE Eng. Med. Biol. Mag., 22(6):43-50 (2003).
Reichle et al., Combined laser tweezers and dielectric field cage for the analysis of receptor-ligand interactions on single cells, Electrophoresis, 22(2):272-82 (2001).
Romani et al., Capacitive sensor array for localization of bioparticles in CMOS lab-on-a-chip, Proc. Int. Solid State Circuit Conference, 1:224-5 (2004).
Rousselet et al., Directional motion of brownian particles induced by a periodic asymmetric potential, Nature, 370(6489):446-8 (1994).
Schnelle et al., Three-dimensional electric field traps for manipulation of cells—calculation and experimental verfication, Biochem. Biophys. Acta, 1157(2):127-40 (1993).
Stoecklein et al., Direct genetic analysis of single disseminated cancer cells for prediction of outcome and therapy selection in esophageal cancer, Cancer Cell, 13:441-53 (2008).
Suehiro, The dielectrophoretic movement and positioning of a biological cell using a three-dimensional grid electrode system, J. Phys. D: Appl. Phys., 31:3298-305 (1998).
Zieglschmid et al., Detection of disseminated tumor cells in peripheral blood, Crit. Rev. Clin. Lab. Sci., 42(2):155-96 (2005).
Corver et al., High-resolution multiparameter DNA flow cytometry for the detection and sorting of tumor and stromal subpopulations from paraffin-embedded tissues, Curr. Protoc. Cytom., Chapter 6, Unit 6.27 (2009).
Vona et al., Isolation by size of epithelial tumor cells : a new method for the immunomorphological and molecular characterization of circulatingtumor cells, Am. J. Pathol., 156(1):57-63 (2000).
Office Action (English translation), Japanese patent application No. 2014-549623, dated Jun. 7, 2016.

\* cited by examiner

DEVICES, APPARATUS, KIT AND METHOD FOR TREATING A BIOLOGICAL SAMPLE

CROSS-REFERENCE TO RELATED APPLICATIONS

This is the U.S. national phase of International Application No. PCT/IB2012/057797, filed Dec. 28, 2012, which claims the benefit of Italian Patent Application No. BO2011A000766, filed Dec. 28, 2011.

TECHNICAL SECTOR

The present invention concerns a hollow device, a covering device, an apparatus, a kit and a method for treating a sample.

BACKGROUND TO THE INVENTION

It is known that biological samples are treated in different ways in order to obtain the isolation of particular types of particles (normally, cells).

Examples in this regard are the devices and methods described in the patent applications PCT/IB2010/000615 PCT/IB2010/000580 (relative to the DEPArray™ system).

Usually, at the end of the above-mentioned treatments, samples are obtained in which the particles are inserted at low concentrations in a liquid component. In this regard, it should be noted that the liquid component is normally a buffer, which cannot be used in subsequent analysis steps, and the volume of the samples is usually too high. For example, the samples obtained following use of the DEPArray™ system have volumes of approximately 38 μL, whereas subsequent steps (like WGA—Whole Genome Amplification) require volumes lower than 1 μL.

The samples therefore have to be treated by centrifugation at high speed and an operator has to very carefully withdraw the excess liquid manually using a pipette (and slanting the test tube containing the sample). There are many problems connected with this procedure, including:

- the success of the operations depends largely on the ability of the operator; there is a risk, which can be high if the operator does not operate correctly, of removing the particle together with the excess liquid. The success rate of the procedure is not reliable and cannot always be reproduced, and depends on the type of buffer used;
- the operations are relatively slow;
- the procedure requires particular care, such as the use of dedicated pipettes and contamination-free tips with dual filter to reduce the risk of the sample becoming contaminated during handling by the operator;
- there is a relatively high risk of the particle/s being damaged due to the centrifugation which, as mentioned, is performed at relatively high speeds (therefore imparting a relatively high stress to the particle/s).

The object of the present invention is to provide a hollow device, a covering device, an apparatus, a kit and a method which overcome, at least partially, the drawbacks of the known art and if possible are, at the same time, easy and inexpensive to produce.

SUMMARY

According to the present invention, a hollow device, a covering device, an apparatus, a kit and a method are provided as described in the following independent claims and, preferably, in any one of the claims depending directly or indirectly on the independent claims.

BRIEF DESCRIPTION OF THE DRAWINGS

The invention is described below with reference to the accompanying drawings, which illustrate some non-limiting embodiment examples thereof, in which.

EMBODIMENTS OF THE INVENTION

Figure 11:
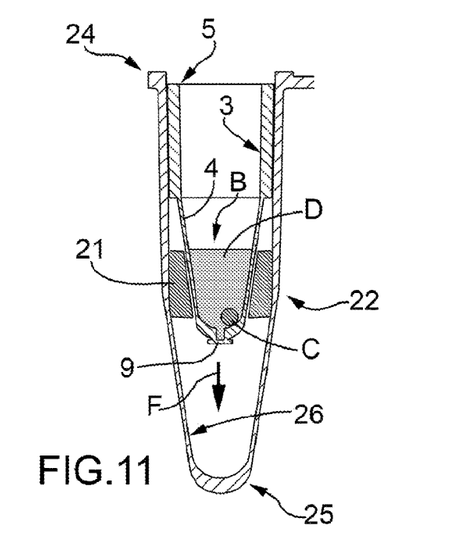
Figure 12:
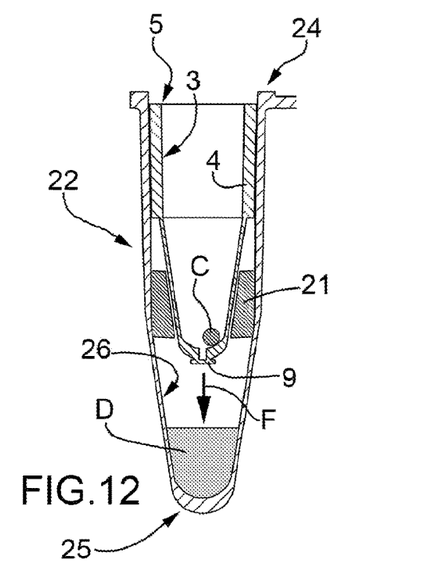
Figure 13:
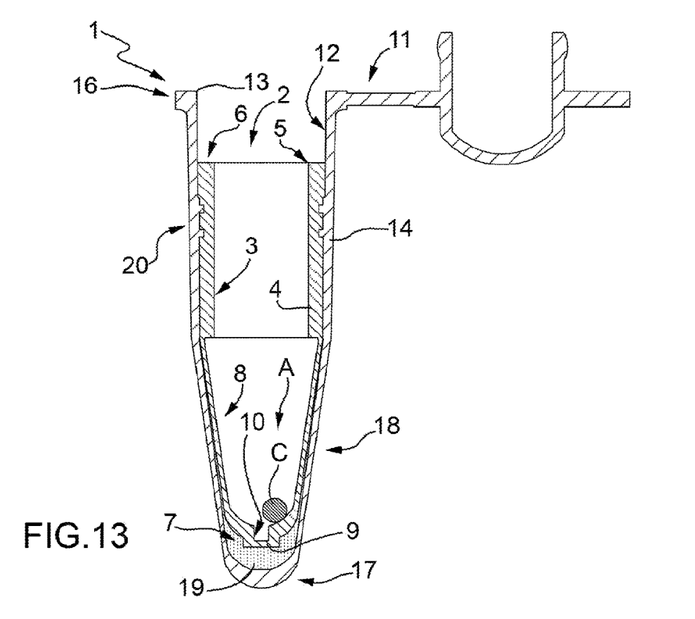
Figure 14:
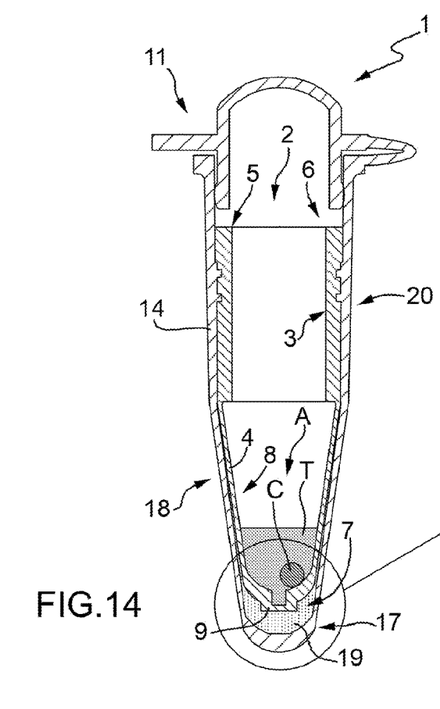
Figure 15:
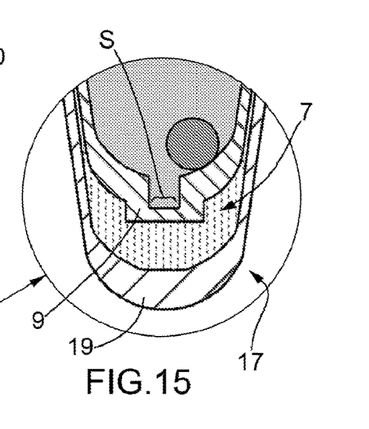
FIG. 15 is an enlarged scale view of a detail of FIG. 14.

In FIGS. 1 to 5 and 10 to 14, the number 1 indicates as a whole an apparatus for the treatment of a sample A (biological) (see, in particular, FIGS. 13 and 14).

Figures 1, 2, 3, 4, 5:
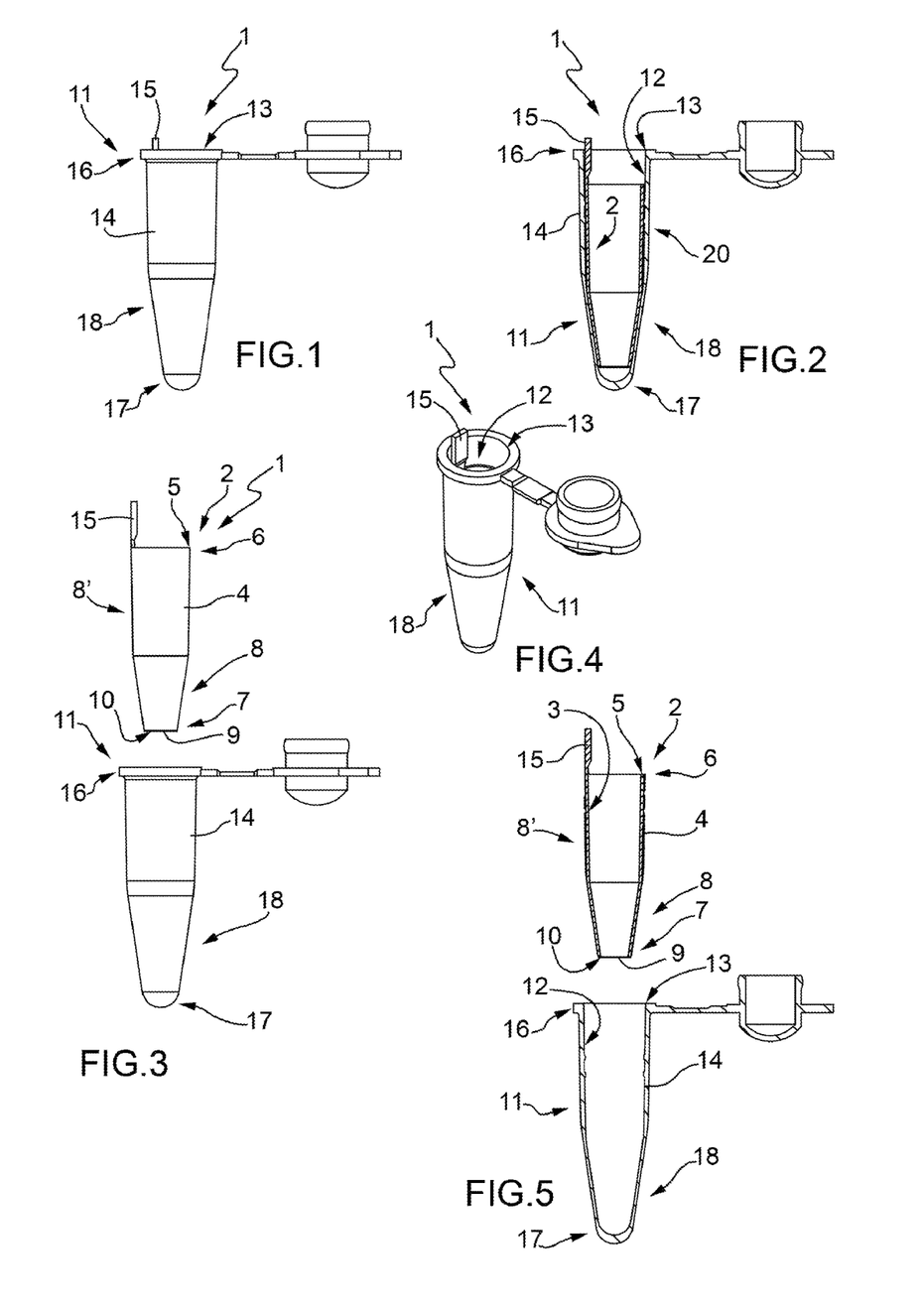
FIG. 1 is a lateral view of an apparatus produced according to the present invention.
FIG. 2 is a lateral section of the apparatus of FIG. 1.
FIG. 3 is a view of the apparatus of FIG. 1 in a different operating configuration.
FIG. 4 is a perspective view of the apparatus of FIG. 1.
FIG. 5 is a lateral section of the view of FIG. 3.
Figure 6:
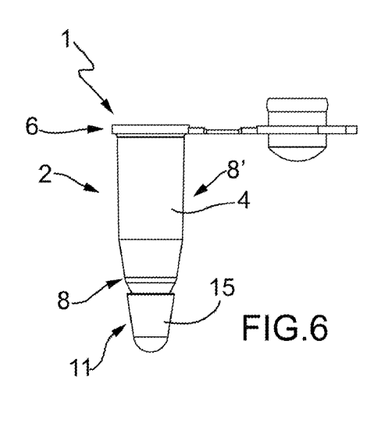
FIG. 6 is a lateral view of a further embodiment of an apparatus produced according to the present invention.
Figure 7:
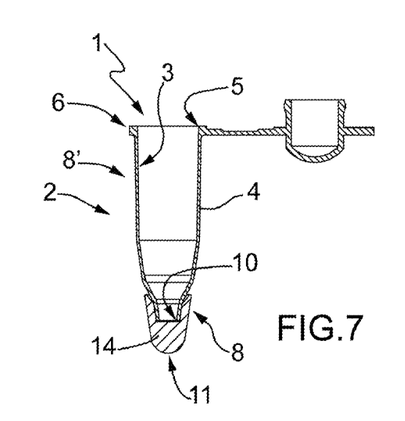
FIG. 7 is a lateral section of the apparatus of FIG. 6.
Figure 8:
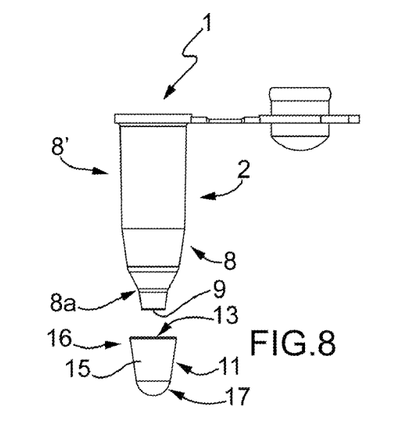
FIG. 8 is a view of the apparatus of FIG. 6 in a different operating configuration.
Figure 9:
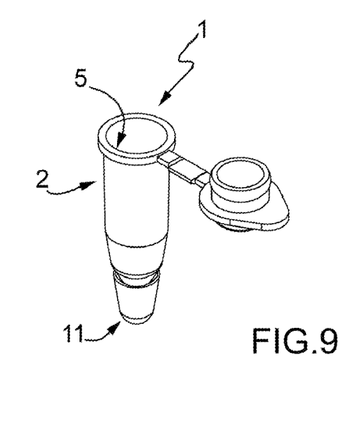
FIG. 9 is a perspective view of the apparatus of FIG. 6.

The apparatus 1 is used to amplify (for example by means of PCR/RT-PCR) the (part of the) DNA/RNA contained in the sample A, for example by means of a PCR machine (known per se and not illustrated), inside which the apparatus 1 is inserted.

According to one aspect of the present invention, a hollow device 2 is provided. The hollow device 2 is suited to the treatment of a sample B (biological) and/or of the above-mentioned sample A.

In particular, the sample B (FIGS. 10 and 11) comprises at least one particle (advantageously, at least one cell) C and a liquid component D (more precisely, a buffer, in which the cell is immersed). The sample A (in particular, FIGS. 13 and 14) is obtained by concentration of the sample B; also the sample A therefore comprises at least the particle C.

In the present text, by particle we mean a corpuscle having the largest dimension of less than 1000 μm (advantageously less than 100 μm). Non-limiting examples of particles are: cells, cell debris (in particular, cell fragments), cell aggregates (for example small clusters of cells deriving from stem cells such as neurospheres or mammospheres), bacteria, liposheres, microspheres (in polystyrene and/or magnetic) and microspheres linked to cells. Advantageously, the particles are cells.

According to some embodiments, the particles have the smallest dimension greater than 1 μm.

In the present text, by dimensions of a particle we mean the length, width and thickness of the particle.

The apparatus 1 comprises (see, in particular, FIGS. 5 and 13-15) the hollow device 2. The hollow device 2 in turn has an inner chamber 3; a wall 4, which delimits the inner chamber 3; and an opening 5, which establishes a communication between the inner chamber 3 and the external environment. The inner chamber 3 is suited to house the above-mentioned sample A (and/or B).

Figure 10:
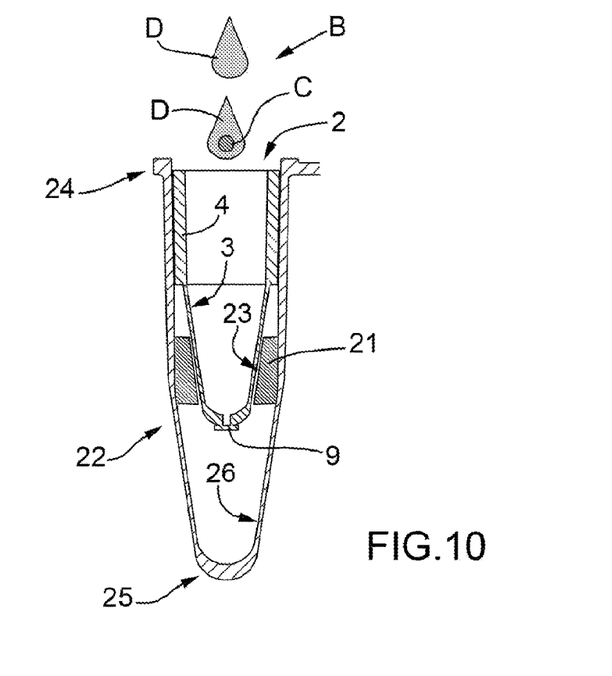
FIGS. 10 to 14 schematically show different steps of use of a device, part of the apparatus of FIG. 1, according to the present invention.

It should be noted that the hollow device 2, in addition to being used as part of the apparatus 1, is also used to separate the particle C and the liquid component D from each other (FIGS. 10-12). In this way, sample A is obtained (concentrated with respect to sample B—FIG. 12) which is the one actually treated by means of the apparatus 1 (FIGS. 13 and 14).

In particular, the hollow device 2 has an elongated (cylindrical) shape; an end 6, in the area of which the opening 5 is arranged; and a closed end 7 (which is opposite the end 6). More precisely, the hollow device 2 has a substantially tubular shape (with one closed end). The inner chamber 3 has substantially circular transverse sections.

Advantageously, the hollow device 2 comprises at least a part (which is also hollow) tapered (towards the end 7). More precisely, the part 8 has substantially the shape of a truncated cone. Analogously, the inner chamber 3 comprises at least one tapered part (towards the end 7). More precisely, the inner chamber 3 has substantially the shape of a truncated cone (in the area of the part 8). The end 7 is also an end of the part 8.

According to some embodiments, the hollow device 2 comprises a part 8', which is integral with the (more precisely is in one piece with the) part 8, is substantially tubular (cylindrical) and has a substantially constant transverse section (or with a lower degree of tapering than the degree of tapering of the part 8). The end 6 is also an end of the part 8'.

According to alternative non-illustrated embodiments, the hollow device 2 does not comprise the part 8' (in other words, the hollow device 2 consists of the part 8). In these cases, the part 8' is a separate device which can be added to the hollow device 2 for certain steps of the treatment of the sample A (and/or B). For example, the part 8' can be added during a step of genetic amplification (for example by means of PCR) when the hollow device 2 is part of the apparatus 1 in order to maintain the hollow device 2 in a substantially fixed position (as illustrated in FIG. 14, for example).

The inner chamber 3 has substantially circular transverse sections.

The inner chamber 3 has transverse sections with area from 10 mm$^2$ to 80 mm$^2$ (in particular, from 20 mm$^2$ to 35 mm$^2$).

The hollow device 2 also comprises a filter 9 which is arranged in the area of the end 7 and separates the inner chamber 3 from the external environment. The filter 9 has a porosity via which, in use, at least part of the liquid component D of the sample B can pass through the filter 9 (coming out of the inner chamber 3), with the particle C not being allowed to pass through the filter 9. Advantageously, the filter 9 substantially does not allow the passage of DNA/RNA fragments.

The filter 9 has pores with diameters up to 1 µm; specifically, the filter 9 does not have pores with diameters greater than 1 µm. Advantageously, the filter 9 has pores with diameters up to 600 nm; specifically, the filter 9 does not have pores with diameters greater than 600 nm. Advantageously, the filter 9 has pores with diameters up to 500 nm; specifically, the filter 9 does not have pores with diameters greater than 500 nm. Advantageously, the filter 9 has pores with diameters up to 450 nm; specifically, the filter 9 does not have pores with diameters greater than 450 nm.

In particular, the filter 9 has pores with diameters of at least 2 nm (more precisely, at least 15 nm); specifically, the filter 9 has the majority of pores with diameters of at least 2 nm (more precisely, at least 15 nm). Advantageously, the filter 9 has pores with diameters of at least 100 nm (more precisely, at least 250 nm); specifically, the filter 9 has the majority of pores with diameters of at least 100 nm (more precisely, at least 250 nm). Advantageously, the filter 9 has pores with diameters of at least 300 nm; specifically, the filter 9 has the majority of pores with diameters of at least 300 mm. More advantageously, the filter 9 has pores with diameters of at least 350 nm; specifically, the filter 9 has the majority of pores with diameters of at least 350 mm.

According to some embodiments, the filter 9 does not have pores with diameters smaller than 2 nm (more precisely, smaller than 15 nm; advantageously, smaller than 100 nm; in particular, smaller than 250 nm; more advantageously, smaller than 300 nm; in particular, smaller than 350 nm).

It has been experimentally observed that pores with dimensions smaller than those indicated cause an excessive reduction in the passage of liquid. To obtain outflow of the liquid in a reasonable time, it is necessary to apply a pressure which would damage the particle/s C.

It has also been observed that pores with dimensions greater than those indicated involve the risk of the particle/s C passing through the filter 9 and dispersing. Therefore, the dimension of the pores must be preferably smaller than that of the particles to be retained in the cavity. Furthermore, pores that are too large may cause, in subsequent analysis steps (for example by PCR), the loss of biological material of interest (for example genetic material).

Unless specified to the contrary, in the present text, by diameter of a pore we mean the limiting diameter, i.e. the diameter of a circle having the same area as the smallest (transverse) section of the pore.

In particular, the limiting diameter is determined by means of the method described in ASTM F316-03(2011) (Standard Test Methods for Pore Size Characteristics of Membrane Filters by Bubble Point and Mean Flow Pore Test).

Advantageously, the filter 9 has a thickness of less than 500 µm. According to some embodiments, the filter 9 has a thickness of less than 250 µm (advantageously, less than 100 µm; in particular, less than 50 µm; more precisely, less than 40 µm). In this way, among other things, the passage through the filter 9 is relatively easy and relatively little material can accumulate inside the filter 9.

Advantageously, the filter 9 has a thickness greater than 1 µm (in particular, greater than 10 µm; more precisely, greater than 15 µm). In this way, among other things, the filter 9 has sufficient mechanical strength and is able to operate correctly.

Advantageously, the filter 9 has a hold-up volume, i.e. the volume of liquid that can be contained inside the filter 9, of less than 2 µL (advantageously, less than 1 µL).

In this regard, it should be noted that for a high hold-up volume, higher than the starting volume specified for the desired nucleic acid analysis procedure (e.g. DNA or RNA), the reaction volumes would have to be reduced to maintain in specification the concentration of the active reagents, at least in the first steps of the procedure. This can make the reaction inefficient.

In particular, the hold-up volume is measured as follows: an initial known volume of solution is placed in the hollow device 2; the hollow device 2 is arranged in a discharge element 22 (described and illustrated below in FIGS. 10 to 12); it is centrifuged (approximately 2000 rpm for two minutes) so that there is no more solution in the inner chamber 3; the volume of liquid collected is measured and the volume measured is subtracted from the initial volume.

The filter 9 comprises (in particular, is composed of) a material chosen from the group consisting of: PC (polycarbonate), PP (polypropylene), polyethersulfones (PES), polyethylene (PE), PVDF (polyvinylidene fluoride), nylon, silicon, $SiO_2$, silicon nitride, fibreglass or a combination thereof.

According to some embodiments, the filter 9 comprises (in particular, is composed of) a material chosen from the group consisting of: PC (polycarbonate), PP (polypropylene), polyethersulfones (PES), PVDF (polyvinylidene fluoride), nylon, silicon, $SiO_2$, silicon nitride, fibreglass or a combination thereof.

According to some embodiments, the filter 9 comprises (in particular, is composed of) an organic polymer.

Advantageously, the filter 9 is made of a material that does not allow the DNA (or RNA) to become attached. In particular, the filter 9 does not contain aluminium oxide.

Advantageously, the filter 9 comprises (in particular, is composed of) a material chosen from the group consisting of: PC, (PES). In particular, the filter 9 comprises (in particular, is composed of) PC.

According to some specific embodiments, the filter 9 comprises (in particular, is composed of) Nuclepore™ (a polycarbonate membrane) and/or Supor® (a PES membrane).

The inner chamber 3 has a volume up to 2 mL (advantageously up to 1 mL; in particular, up to 0.5 mL; more precisely, up to 0.2 mL). Advantageously, the inner chamber 3 has a volume of at least 40 µL (in particular, at least 50 µL; more precisely, at least 60 µL).

The opening 5 has an area of at least 9 mm² (advantageously, at least 12 mm²; in particular, at least 18 mm²). According to some embodiments, the opening 5 has an area up to 80 mm² (advantageously, up to 70 mm²; in particular, up to 18 mm²).

The wall 4 has a further opening 10, which is arranged corresponding to the end 7. In particular, the opening 10 is opposite the opening 5. The opening 10 has an area of at least 0.2 mm² (advantageously, at least 0.7 mm²; in particular, at least 2.5 mm²). The opening 10 has an area up to 13 mm² (in particular up to 7 mm²).

The filter 9 is arranged in order to substantially completely cover the opening 10. Advantageously, the filter 9 has an area S (FIG. 15) facing the inner chamber 3 of up to 12.6 mm² (in particular, up to 10 mm²). This is particularly advantageous when the hollow device 2 is used for steps of PCR. In these cases, the volume of solution is relatively small and, therefore, a large area S of the filter 9 would lead to an excessive distribution of the solution on the surface S. This would reduce the efficiency of the PCR.

In some cases, the area S is at least 0.1 mm² (advantageously, at least 0.7 mm²; in particular, at least 1.2 mm²).

The dimensions indicated in this text can be measured with profilometers.

Advantageously, the filter 9 is securely connected to the wall 4. In particular, the connection between filter 9 and wall 4 is provided by one of the following techniques: thermal bonding, solvent bonding, ultrasound bonding), laser bonding, gluing, mechanical interlocking or a combination thereof.

Advantageously, the wall 4 has a thermal conductivity of at least 0.08 W/mK (in particular, at least 0.12 W/mK).

Conductivities above these limits are useful for allowing correct performance of treatment steps of the sample A which entail the production of heat (for example the PCR).

According to some embodiments, the wall 4 has a thermal conductivity up to 0.7 W/mK (in particular, up to 0.2 W/mK).

The thermal conductivity is measured according to the common technical standards. In particular, the thermal conductivity is measured according to the methodology established by ISO 22007. It should be noted that the measurements performed according to this standard are substantially compatible with those performed in accordance with ASTM 1225-09.

Advantageously, the wall 4 has a thickness up to 700 µm (in particular, up to 600 µm). More precisely, the wall 4 has a thickness up to 520 µm (in particular, up to 450 µm). Thicknesses below these limits are useful for allowing correct performance of treatment steps of the sample A which entail the production of heat (for example the PCR).

According to some embodiments, the wall 4 has a thickness of at least 40 µm (in particular, at least 170 µm). More precisely, the wall 4 has a thickness of at least 200 µm (in particular, at least 250 µm).

It is important to underline that, advantageously, the hollow device 2 is (dimensionally and structurally) suited to be used in standard PCR machines.

In this regard, we underline that, advantageously, the materials and the roughness are chosen so as to avoid the absorption of DNA/RNA fragments. The materials are chosen so as not to prevent WGA processes. The materials are chosen so as to withstand high temperatures (greater than 100° C.), such as those reached during the PCR thermal cycles.

In particular, it should be noted that the hollow device 2 can be obtained by cutting (and removing) the upper part of a test tube for PCR and the tip of the test tube. The hole (opening 4) obtained corresponding to the tip is closed by a membrane (which therefore acts as a filter 9) connected to the test tube by means of thermal bonding.

FIGS. 6 to 9 illustrate an alternative embodiment of the apparatus 1 and the hollow device 2. More precisely, the hollow device 2 (of the FIGS. 6-9) is substantially identical to the hollow device 2 described above with reference to FIGS. 1 to 4 and 10 to 14 and differs from it only in the shape of the part 8. The part 8 has an end portion 8a (arranged corresponding to the end 7) with reduced section.

According to one aspect of the present invention, a covering device 11 is provided.

With particular reference to FIGS. 1 to 4, the apparatus 1 furthermore comprises the covering device 11. The covering device 11 is suited to preventing the outflow of liquid from the hollow device 2. In particular, the covering device 11 is suited to preventing the passage of liquid through the opening 10. More precisely, the covering device 11 is suited to fluid-tight coupling with the end 7.

The covering device 11 is (therefore) suited to coupling with the hollow device 2 so as to substantially obstruct the filter 9. In this way, the passage of material (in particular, biological material such as DNA/RNA fragments) from the inner chamber 3 to the outside through the filter 9 is substantially prevented.

As can be noted from the figures, the covering device 11 can be combined with the hollow device 2 so as to obtain the apparatus 1 (FIGS. 1, 2 and 4) or be separated from the hollow device 2 (FIGS. 3 and 5).

More precisely, the covering device 11 has a cavity 12 provided with an opening 13 (in particular, an open end). The cavity 12 is shaped so that it is suited to housing at least part (in some cases, all) of the hollow device 2. In particular, the cavity 12 has a shape which is substantially complementary to the outer shape of the hollow device 2.

The covering device 11 also comprises an outer wall 14 which delimits the cavity 12.

More precisely, the cavity 12 is shaped so that (when the hollow device 2 is housed in the cavity 12) the wall 14 is (substantially completely) in contact with the hollow device 2 (in particular, with the walls 4 and 8).

Advantageously, the wall 14 has a thermal conductivity of at least 0.08 W/mK (in particular, at least 0.12 W/mK). Conductivities higher than these limits are useful for allowing the correct performance of treatment steps of the sample A which entail the production of heat (for example the PCR).

According to some embodiments, the wall 14 has a thermal conductivity up to 0.7 W/mK (in particular, up to 0.2 W/mK).

Advantageously, the wall 14 has a thickness up to 700 μm (in particular, up to 600 μm). More precisely, the wall 14 has a thickness up to 520 μm (in particular, up to 450 μm). Thicknesses below these limits are useful for allowing the correct performance of treatment steps of the sample A which entail the production of heat (for example the PCR).

According to some embodiments, the wall 14 has a thickness of at least 40 μm (in particular, at least 170 μm). More precisely, the wall 14 has a thickness of at least 200 μm (in particular, at least 250 μm).

It is important to underline that, advantageously, the covering device 11 is (dimensionally and structurally) suited to use in standard FOR machines.

The cavity 12 has a volume up to 2 mL (advantageously up to 1 mL; in particular, up to 0.5 mL; more precisely, up to 0.2 mL). Advantageously, the cavity 12 has a volume of at least 40 μL (in particular, at least 50 μL; more precisely, at least 60 μL).

In the embodiment of FIGS. 1 to 6, the cavity 12 is suited to housing (FIGS. 3 and 5) and houses (FIGS. 1, 2 and 4) the entire hollow device 2. In this case, the hollow device 2 comprises a gripping device 15 (in particular, a tab, which is suited to facilitating insertion into and/or extraction from the cavity 12).

According to the embodiment illustrated in FIGS. 6 to 9, the cavity 12 is suited to housing (FIG. 8) and houses (FIGS. 6, 7 and 9) only a portion of the hollow device 2 (in particular, the portion 8a).

Through the opening 13, in use, the hollow device 2 (or a part thereof) is inserted into the cavity 12. The opening 13 is arranged corresponding to one end 16 of the covering device 11.

In particular, the covering device 11 has an elongated (cylindrical) shape and a closed end 17 (which is opposite the end 16). When at least part of the hollow device 2 is inserted in the cavity 12, the end 7 is arranged corresponding to the end 17.

More precisely, the covering device 11 has a substantially tubular shape (with one end closed). The cavity 12 has substantially circular transverse sections.

Advantageously, the covering device 11 comprises at least one part 18 (which is also hollow) tapered (towards the end 17).

More precisely, the part 18 has substantially the shape of a truncated cone. Analogously, the cavity 12 comprises at least one tapered part (towards the end 17). More precisely, the cavity 12 has substantially the shape of a truncated cone (corresponding to the part 18). The end 17 is also an end of the part 18.

Advantageously, the covering device 11 also comprises at least one adjustment element 19.

The adjustment element 19 is arranged in the cavity 12. The adjustment element 19 is (among other things) suited to changing its shape so as to adapt the shape of the cavity 12 to the shape of the hollow device 2 in order to reduce the presence of air between the hollow device and the coupling device. In this way, the transfer of heat from and towards the outside is improved. This is particularly useful when performing genetic amplifications involving cycles that raise the temperature.

In particular, the adjustment element 19 is arranged corresponding to the end 17 (and, therefore, is suited to changing its shape so as to adapt to the shape of the end 7).

The adjustment element 19 is (also) suited to preventing the passage of liquid through the filter 9 (or the opening 10). More precisely, the adjustment element 19 is suited to fluid-tight coupling with the filter 9 (or with the opening 10).

Advantageously, the adjustment element 19 has a thermal conductivity of at least 0.08 W/mK (in particular, at least 0.12 W/mK). Conductivities higher than these limits are useful for allowing the correct performance of treatment steps of the sample A which entail the production of heat (for example the PCR). According to some embodiments, the adjustment element 19 has a thermal conductivity up to 0.7 W/mK (in particular, up to 0.2 W/mK).

Advantageously, the adjustment element 19 comprises (in particular, is composed of) a material chosen from the group consisting of: elastic, elasto-plastic and liquid materials.

According to some embodiments, the adjustment element 19 comprises (in particular, is composed of) a material chosen from the groups consisting of: silicones, rubbers (natural), polymers (synthetic), lubricants, oils or a combination thereof. In some cases, the adjustment element 19 comprises (in particular, is composed of) a material chosen from the group consisting of silicones and oils.

In particular, the silicones (rubbers and polymers) have a hardness of at least 10 (more precisely, at least 15) Shore A. The silicones (rubbers and polymers) have a hardness up to 80 (more precisely, at least 70). The oils (and lubricants) have a viscosity from 1 mPa·s to 10000 Pa·s.

The hardness is measured according to the common standard techniques. In particular, the hardness is measured according to the method established by ISO 868.

The viscosity is measured according to the common standard techniques. In particular, the viscosity is measured according to the method established by ISO 3104. It should be noted that the measurements performed according to this standard are substantially compatible with those performed according to ASTM D445.

In some cases, the oils (and lubricants) have a density from 0.05 g/ml to 10 g/ml. More precisely, by oil we mean a mineral oil (in particular, an oil for PCR).

According to the embodiment illustrated in FIGS. 6 to 9, the function of the adjustment element is performed directly by the wall 14 which is shaped so as to adapt to the hollow device 2 (more precisely, to the part 8 and to the relative portion 8a).

With particular reference to FIGS. 13 and 14, it should be noted that the covering device 11 comprises at least one retaining element 20 to maintain the hollow device 2 in position inside the cavity 12.

The retaining element 20 comprises one or more projections which protrude from the wall 14 (towards the inside of the cavity 12) and are suited to coming into contact with the wall 4.

According to some embodiments, the wall 4 has one or more recesses, which are suited to being engaged by the projections of the retaining element 20. Alternatively or in addition, the wall 4 has protrusions (not illustrated) suited to coupling with the wall 14 (in particular, with the retaining element 20). In this way, the hollow device 2 is securely locked inside the cavity 12.

According to a further aspect of the present invention, a kit is provided comprising the hollow device 2 and the covering device 11.

Advantageously, the kit also comprises an adaptor 21 (FIGS. 10 to 12), which is suited to maintaining in position the hollow device 2 inside a discharge element 22 (in particular, a relatively large test tube). The adaptor 21 has a tubular shape (in particular, annular) and an inner aperture 23 suited to receiving part of the hollow device 2.

In particular, the adaptor 21 is suited to coupling with and locking by contact the wall 4. The adaptor is also suited to be inserted in the discharge element 22 and to lock in contact with an inner surface of said element 22.

Advantageously, the kit also comprises the discharge element 22.

The element 22 has a substantially tubular shape with an open end 24, a closed end 25 and a housing 26 (for the hollow device 2 and the adaptor 21).

According to a further aspect of the present invention, a method is provided for treating the sample (biological) B (in particular, comprising at least a particle C and a liquid component D). The sample B is defined according to the above description in relation to the apparatus 1 and the hollow device 2.

The method comprises an insertion step, during which the sample B is inserted into the hollow device 2. According to the illustrations in FIGS. 10 and 11, during the insertion step, the hollow device 2 is arranged inside the discharge element 22.

According to embodiments not illustrated, the hollow device 2 is arranged externally to the element 22, during the insertion step. In this case, after the insertion step, the hollow device 2 is positioned inside the element 22 (as shown in FIG. 11).

The method also comprises a concentration step (FIGS. 11 and 12), during which a force (in the direction of the arrow F) is applied to the sample B inserted in the hollow device 2 towards the filter 9 so that at least part of the liquid component D passes through the filter 9 and the particle C remains in the inner chamber 3, thus obtaining the sample A (concentrated). The part of the liquid component D which passes through the filter 9 is deposited in the area corresponding to the end 25.

According to some embodiments, the concentration step is achieved by applying a centrifugal force to the sample B. In said case the hollow device 2 (and the element 22) is rotated about an axis (transverse to the longitudinal axis of the hollow device 2).

It should be noted that the force applied is relatively low. In this way the risks of damaging the particle C are low. In particular, it is sufficient to rotate the hollow device to approximately 300 g (2000 rpm).

After the concentration step, the hollow device 2 is removed from the element 22 and coupled with (in particular, inserted in) the covering device 11 so as to substantially obstruct said filter 9 and prevent the passage of material (in particular, fragments of DNA/RNA) from the inner chamber 3 to the outside through the filter 9. In this way, the apparatus 1 is obtained.

At this point, further treatment steps of the sample A are performed and, more precisely, the particle C undergoes the treatments necessary to obtain a genetic amplification (for example by means of PCR). In particular, as the first further step, a buffer T suited to the purpose is inserted in the hollow device (FIG. 14).

The information disclosed in the present text can be used downstream of various types of treatment of biological material, for example:
  sorting by DEPArray™;
  other types of sorting processes (micromanipulation, optical tweezers, laser micro-dissection etc.);
  Fluorescence Activated Cell Sorting—FACS;
  dispensing with pipette;
  dispensing with syringe.

Furthermore, the information disclosed in the present text can be used upstream of various types of treatment, for example:
  whole genome amplification (WGA)
  whole transcriptome amplification—WTA;
  polymerase chain reaction—PCR;
  fixing, permeabilization and staining or a combination thereof.

It is important to underline that the content of the present text offers significant advantages with respect to the state of the art. The advantages include the following:
  the operations are very rapid and simple (this also reduces, among other things, the risk of contamination);
  the hollow device 2 is always used; it is therefore not necessary to carry out risky transfers of samples (due both to the risk of damaging or losing the sample and the risk of contamination);
  the results are reproducible (they do not depend on the ability of the operator);
  the operations are "kind": the sample (and, in particular, the cell) is handled delicately without the need to apply high forces.

Unless explicitly indicated otherwise, the content of the references (articles, books, patent applications etc.) cited in this text is here referred to in full. In particular the above-mentioned references are incorporated here for reference.

Further characteristics of the present invention will be illustrated in the following description of two merely illustrative non-limiting examples.

Example 1

An approximately 150 µL hollow device 2 was inserted in a 2 mL test tube (Eppendorf) provided with adaptor 21 in order to obtain a structure analogous to the one illustrated in FIG. 10. A 38 µl sample containing a buffer and a cell was inserted in the hollow device 2. The test tube was closed and underwent centrifugation for two minutes at 2000 rpm (substantially as illustrated in FIGS. 11 and 12).

The hollow device 2 was extracted and inserted in a covering device 11 (more precisely, a 200 µL test tube for PCR) containing a few microliters of oil for PCR. The 2 mL test tube (Eppendorf) was discarded.

At this point, the contents of the device underwent amplification of the whole genome by means of the AmpliI™ WGA kit (Silicon Biosystems) and STR (Short Tandem Repeat) analysis.

The procedure was repeated 10 times and the results with Allele Call Rate were above 90% in all cases.

The known procedure was also performed, under which 10 samples like those described above (38 µl samples each containing a buffer and a cell) were treated by centrifugation at high speed and an experienced operator manually withdrew, with great care and attention, the excess liquid using a pipette (and slanting the test tube containing the sample). In this case only 9 of the 10 tests performed produced results with Call Rate above 90%. Also the time taken in these cases was significantly longer than the time taken using the hollow device 2.

The invention claimed is:

1. A hollow device for treating a biological sample by separating at least a particle and at least part of a liquid from each other, comprising:
   an inner chamber, which has a volume up to 2 mL;
   a first end;
   a first opening, which is arranged in the area of the first end, and establishes access to the inner chamber from outside the inner chamber, and the first opening has an area of at least 9 mm$^2$;
   a second end defining a second opening, wherein the liquid flows out from the inner chamber through the second opening; and
   a filter, which is arranged in the area of the second end and extends across a surface of the second opening exterior to the inner chamber, separates the inner chamber from the outside, has pores with diameters ranging from 2 nm to 1 µm, an area facing the inner chamber of up to 12.6 mm$^2$, and a thickness up to 500 µm; and
   at least one wall, which delimits the inner chamber and has a thermal conductivity from 0.08 W/mK to 0.7 W/mK, wherein the at least one wall has a thickness up to 700 µm in at least a region of the at least one wall upstream of the filter and the second end.

2. The hollow device according to claim 1, wherein the filter has a hold-up volume of less than 2 µL and the area facing the inner chamber is at least 0.1 mm$^2$.

3. The hollow device according to claim 1, wherein:
   the second opening has an area from 0.2 mm$^2$ to 13 mm$^2$;
   the filter has a thickness from 1 µm to 250 µm and covering in a substantially complete manner the second opening;
   the inner chamber has transverse sections with areas from 10 mm$^2$ to 80 mm$^2$; and
   the pores have diameters ranging from 250 nm to 600 nm.

4. The hollow device according to claim 1, wherein the hollow device has a substantially tubular shape and, at least partially, the shape of a truncated cone.

5. A covering device externally coupled to the hollow device according to claim 1, so as to substantially obstruct said filter and prevent material from passing from the inner chamber to the outside through the filter, the covering device comprising:
   a cavity, which is provided with an open end, which is suited to allow the hollow device to be inserted into the cavity, and with a closed end; and an adjustment element that is adapted to change to adjust to the shape of the hollow device.

6. The covering device according to claim 5, wherein the cavity is shaped so as to house at least part of the hollow device; the adjustment element is arranged in the area of the closed end and adapted to change shape to reduce the presence of air between the hollow device and the covering device.

7. The covering device according to claim 5, wherein the adjustment element comprises a material selected from the group consisting of elastic materials, elasto-plastic materials, and liquid materials.

8. The covering device according to claim 7, wherein the adjustment element comprise a material selected from the group consisting of silicone, natural rubbers, synthetic polymers, lubricants, oil, and combinations thereof; and wherein the silicone, the rubbers, and the polymers each has a hardness ranging from 10 to 80 Shore A; and the oil and the lubricants each have a density ranging from 0.05 g/ml to 5 g/ml and a viscosity ranging from 1 mPa s to 10000 Pa s.

9. The covering device according to claim 5, further comprising at least an outer wall, which at least partially delimits the cavity and has a thermal conductivity from 0.08 W/mK to 0.7 W/mK and a thickness from 40 µm to 700 µm.

10. An apparatus for treating a sample (A), comprising the hollow device according to claim 1 and a covering device externally coupled to the hollow device so as to substantially obstruct said filter and prevent material from passing from the inner chamber to the outside through the filter, wherein:
    the covering device has a cavity, which is provided with an open end and a closed end; and
    the hollow device is at least partially arranged inside the cavity; the second end being arranged in the area of the closed end.

11. The apparatus according to claim 10, wherein the covering device comprises an outer wall; and the hollow device is arranged in contact with the outer wall.

12. The apparatus according to claim 10, wherein the covering device further comprises an adjustment element that is adapted to adjust to the shape of the hollow device when the covering device is coupled to the hollow device.

13. A method for treating a sample comprising at least one particle and a liquid component, comprising:
    an insertion step, during which the sample is inserted inside the hollow device according to claim 1;
    a concentration step, during which a force is applied to the sample inserted into the hollow body towards the filter, so that at least part of the liquid component passes through the filter and the particle remains in the inner chamber.

14. The method according to claim 13, further comprising a coupling step, which takes place after the concentration step and during which a covering device is coupled to the hollow device so as to substantially obstruct said filter and prevent material from passing from the inner chamber to the outside through the filter; wherein the covering device has a cavity, which is provided with an open end, through which at least part of the hollow device is inserted into the cavity, and with a closed end; the second end being arranged in the area of the closed end.

15. The method according to claim 14, wherein the covering device further comprises an adjustment element that is adapted to adjust to the shape of the hollow device when the covering element is coupled to the hollow device.

16. The method according to claim 13, further comprising a genetic amplification step, which takes place after the coupling step and during which at least part of the nucleic acids of the particle are amplified.

17. A kit comprising the hollow device according to claim 1, and a covering device suited to be externally coupled to the hollow device, so as to substantially obstruct said filter and prevent material from passing from the inner chamber to the outside through the filter; wherein the covering device has a cavity, which is provided with an open end, through which at least part of the hollow device is inserted, in use, into the cavity, and with a closed end; and the cavity is shaped so as to be suited to house at least part of the hollow device.

18. The kit according to claim 17, wherein the covering device further comprises an adjustment element that adjusts to the shape of the hollow device when the covering device is coupled to the hollow device.

19. The hollow device of claim 1, wherein the inner chamber has transverse sections that are substantially circular.

20. An apparatus for treating a sample, comprising:
a hollow device, comprising:
an inner chamber having a volume of up to 2 mL,
a first end,
a first opening arranged in the area of the first end and providing communication between the inner change and the outside, wherein the opening has an area of at least 9 mm²,
a second end
at least one wall, which delimits the inner chamber and has a thermal conductivity from 0.08 W/mK to 0.7 W/mK and a thickness up to 700 μm, and
a filter arranged in the area of the second end, the filter separating the inner chamber from the outside, the filter comprising pores having diameters ranging from 2 nm to 1 μm, an area facing the inner chamber up to 12.6 mm², and a thickness of up to 500 μm; and
a covering device configured to externally couple to the hollow device and substantially obstruct the filter and prevent material from passing from the inner chamber to the outside through the filter when coupled to the hollow device, the covering comprising:
a cavity comprising an open end sized to allow the hollow device to be inserted into the cavity, and a closed end' and
an adjustment element that adjusts to the shape of the hollow device when the covering device is coupled to the hollow device.

21. The hollow device according to claim 1, wherein the filter is disposed on an exterior surface of the hollow device.

22. The hollow device according to claim 1, wherein the one or more walls comprise one lateral wall, having a thickness of up to 700 μm and a thermal conductivity of 0.08 W/mK to 0.7 W/mK; and a bottom wall arranged at the second end and having a thickness greater than the thickness of the lateral wall, and
the second opening is arranged at the bottom wall.

23. A hollow device for treating a biological sample by separating at least a particle and at least part of a liquid from each other, comprising:
one or more walls that cooperate to define an inner chamber extending between oppositely disposed first and second ends;
a first opening defined in the first end, the first opening establishing access to the interior chamber from outside the chamber, wherein the first opening has an area of at least 9 mm²;
a second opening defined in the second end; and
a filter extending across the second opening on a surface exterior to the inner chamber, thereby separating the inner chamber from the outside, wherein:
the inner chamber has a volume up to 2 mL,
the one or more walls have a uniform thickness of up to 700 μm and a thermal conductivity of 0.08 W/mK to 0.7 W/mK, and
the filter has pores with diameters ranging from 2 nm to 1 μm, an area facing the inner chamber of up to 12.6 mm², and a thickness up to 500 μm.

* * * * *